(12) United States Patent
Mehta

(10) Patent No.: US 9,636,449 B2
(45) Date of Patent: May 2, 2017

(54) RINSING ASSEMBLY

(76) Inventor: Ketan C. Mehta, Santa Rosa, CA (US)

( * ) Notice: Subject to any disclaimer, the term of this patent is extended or adjusted under 35 U.S.C. 154(b) by 1067 days.

(21) Appl. No.: 13/525,726

(22) Filed: Jun. 18, 2012

(65) Prior Publication Data
US 2013/0338568 A1 Dec. 19, 2013

(51) Int. Cl.
A61M 31/00 (2006.01)
A61M 3/02 (2006.01)

(52) U.S. Cl.
CPC ........... *A61M 3/0287* (2013.01); *A61M 3/025* (2013.01); *A61M 2210/0662* (2013.01)

(58) Field of Classification Search
CPC ........ A61M 2210/0662; A61M 3/0283; A61M 1/0064; A61M 1/0058; A61M 3/02; A61M 3/0279; A61M 3/0287
USPC .............................. 604/514, 38, 131, 150, 30
See application file for complete search history.

(56) References Cited

U.S. PATENT DOCUMENTS

| 5,527,275 | A | * | 6/1996 | Ginsberg | ................ | A61M 3/02 601/155 |
|---|---|---|---|---|---|---|
| 5,685,851 | A | | 11/1997 | Murphy et al. | | |
| 6,059,803 | A | | 5/2000 | Spilman | | |
| 8,062,216 | B2 | | 11/2011 | Raghuprasad | | |
| 2008/0139888 | A1 | * | 6/2008 | Strom | ................... | A61B 1/227 600/200 |

FOREIGN PATENT DOCUMENTS

| WO | WO 2006/008432 | 1/2006 |
|---|---|---|
| WO | WO 2011/038362 | 3/2011 |

OTHER PUBLICATIONS

Authorized officer Inho Han, International Search Report and Written Opinion in PCT/US2013/045871, mailed Dec. 11, 2013, 12 pages.
Authorized officer Simin Baharlou, International Preliminary Report on Patentability in PCT/US2013/045871, mailed Dec. 31, 2014, 9 pages.

* cited by examiner

Primary Examiner — Phillip Gray

(57) ABSTRACT

An assembly for dispensing fluid is described. In some implementations, an assembly can include a housing containing fluid, where the housing includes a conduit. The assembly can also include an actuator operably attached to the conduit of the housing. The actuator can include a body portion surrounding a cavity; a tip portion having a fluid path that is fluidly connected to the cavity, the cavity being fluidly connected to the conduit, and a channel support including a fluid passage space under pressure. The assembly can further include a collector having a collection zone configured to collect the fluid dispensed by the actuator.

20 Claims, 6 Drawing Sheets

RINSING ASSEMBLY

FIELD

This disclosure relates to fluid dispensing.

BACKGROUND

Earwax, also known as cerumen, is a yellowish waxy substance secreted in the ear canal. Earwax protects the skin of the human ear canal, assists in cleaning and lubrication, and also provides some protection from bacteria, fungi, insects and water. Excess or impacted earwax can press against the eardrum and/or occlude the external auditory canal and impair hearing. Ear rinsing can be used to soften, loosen, and wash out excessive earwax built-up.

SUMMARY

Assemblies, systems and methods for dispensing fluid for rinsing (e.g., ear rinsing) are described. In some implementations, a dispensing assembly coupled with a collection component can be provided for dispensing fluid of a rinsing formula into an orifice (e.g., an ear canal) and collecting the fluids at the end of a rinsing cycle. In some implementations, the dispensing assembly can include a sealed housing containing fluid. The sealed housing can include a conduit. The dispensing assembly also can include an actuator operationally attached to the conduit of the sealed housing. The actuator can include a body portion surrounding a cavity and a tip portion having a fluid path. The fluid path can be fluidly connected to the cavity, and the cavity can be fluidly connected to the conduit. A channel support can be included in the actuator. The channel support can retain a substantial fluid passage space under pressure. The dispensing assembly can further include a collector having a collection zone configured to collect and store used fluid exiting the orifice (e.g., ear canal).

In some implementations, an assembly can be provided that includes a sealed housing containing fluid. The sealed housing can include a conduit and an actuator operationally attached to the conduit of the sealed housing. The actuator can include a body portion surrounding a cavity and a tip portion having a fluid path that is fluidly connected to the cavity wherein the cavity is fluidly connected to the conduit. The actuator can further include a channel support retaining substantial fluid passage space under pressure. The sealed housing can further include a collector having a collection zone configured to collect the fluid.

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

As will be discussed in greater detail below, a rinsing assembly for removing particulates or otherwise clean an orifice (e.g., for removing earwax or other residues in the ear canal) is described. Ear rinsing assemblies typically require a particular entry angle for rinsing fluids to enter ear canals so that the washing fluid can exit without interfering with the incoming fluid. An additional container (or person) may also be needed to assist in collecting the used fluid (e.g., a bucket, bowl, sink, or other types of containers). The rinsing assembly as described herein allows for efficient application of rinsing fluids (e.g., the user may casually insert the assembly into ear without additional aids, such as operation by another person, containers, etc.) and effective rinsing performance (e.g., to facilitate the exiting of the used fluid without interfering with the incoming fluid). While reference is made below to rinsing a human ear, the rinsing assembly proposed may be used to rinse other orifices.

Figure 1:
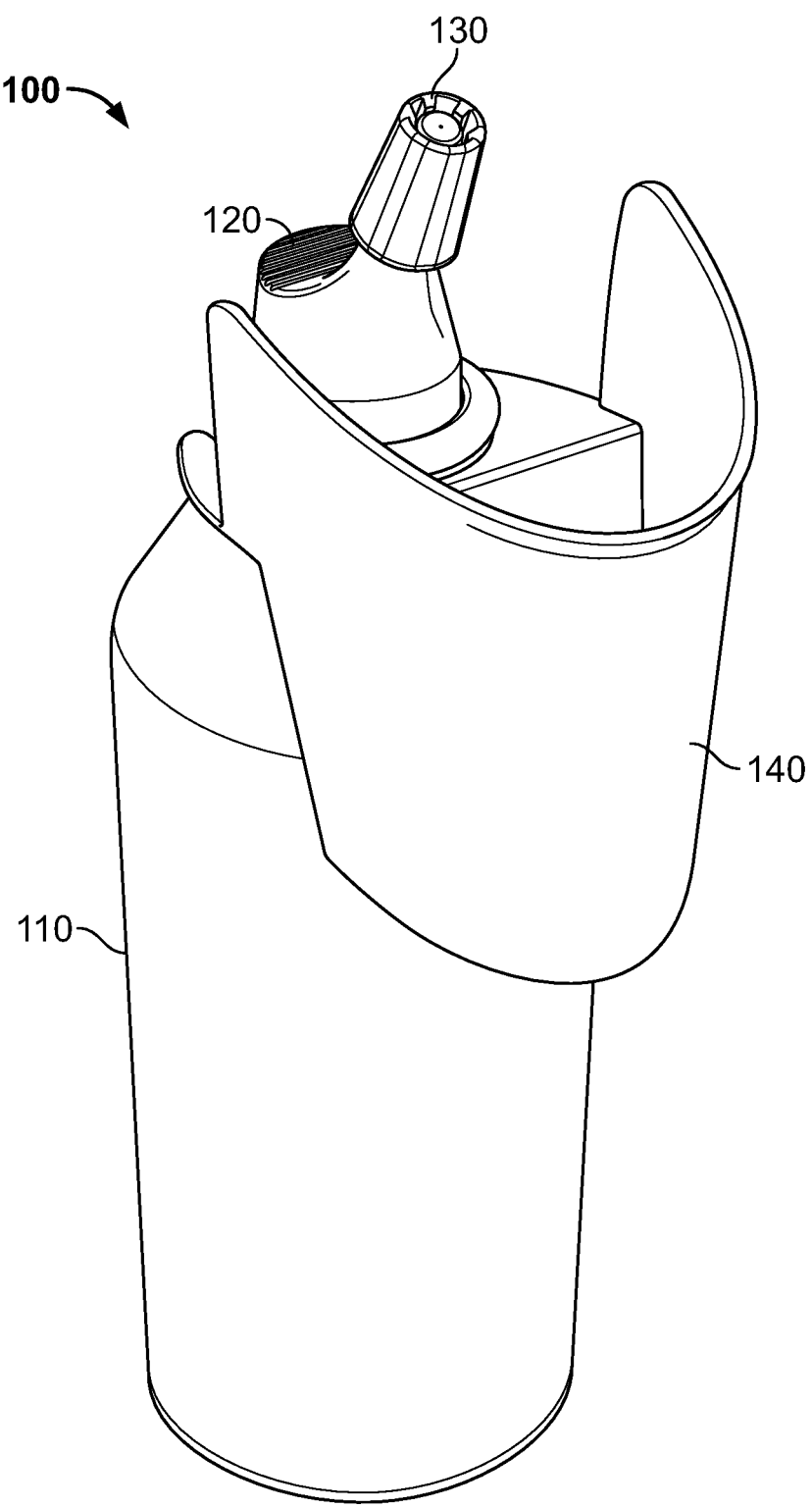
FIG. 1 is a schematic perspective view of a rinsing assembly.

FIG. 1 is a schematic perspective view of a rinsing assembly 100. The rinsing assembly 100 includes a housing (e.g., sealed housing 110), an actuator 120, a channel support 130, and a collector 140. Although not shown, a pair of ear plugs can also be included and used to allow rinsing solution to remain in the ears during the rinsing phase. During a rinsing operation, a user can hold the rinsing assembly 100 at the sealed housing 110. The user can place the rinsing assembly 100, for example, near an ear such that the channel support 130 is partially inserted into the ear canal and the collector 140 is in contact with a side of the user's face/head just under the ear. The collector 140 can be positioned in a manner that conforms to the contour of the user's face such that excessive rinsing fluid may move directly into the collector 140 without spilling. The user can press down the actuator 120 and dispense rinsing fluid into the ear canal. The rinsing fluid can exit through the fluid channels of the channel support 130 (described below and shown in FIG. 7) and be collected (along with used fluid exiting the ear canal) by the collector 140. Although the actuator 120 is shown with a conical shape, other shapes (e.g., cylindrical or shapes that facilitate insertion into a subject's ear) also are contemplated. Although not shown, in some implementations, the channel support 130 can include perforations or materials protruding from a portion of the channel support 130 that function as a "stopper" to prevent the channel support 130 from over-extending or over-inserting into the ear canal that may cause injury to the eardrum. Alternatively, the channel support 130 can be designed with a tapered, conical design that widens from the top to the bottom (e.g., with a size that is larger than a diameter of the ear canal) to prevent the entire channel support 130 from being inserted into the ear canal.

The sealed housing 110 can contain rinsing fluid of various formula. For example, the rinsing fluid carried in the sealed housing 110 can include pure water, sodium chloride, sodium bicarbonate, and other appropriate ingredients. In some implementations the rinsing fluid can include an ear wax removal fluid or compound in addition to a rinsing agent. For example, the rinsing fluid can include a mixture of carbamide peroxide, glycerin, oxyquinoline, aloe barbadensis leaf juice, and chamomile *recutita* (*matricaria*) flower extract. The user of the rinsing system in association with ear wax removal is discussed in greater detail below. The actuator 120 can dispense the rinsing fluid in the sealed housing 110 at an attenuated pressure into a user's ear. For example, the actuator 120 can include a tip portion and a body portion including a cavity. Rinsing fluids exiting the sealed housing can first enter the cavity of the body portion and then be dispensed at the tip portion. The flow rate, as well as the exit pressure, can be attenuated at the cavity and/or the tip portion (e.g., attenuated at various pressure levels). The used rinsing fluid can exit though the channels of the channel support 130 without interfering with the incoming rinsing fluid.

Figure 2:
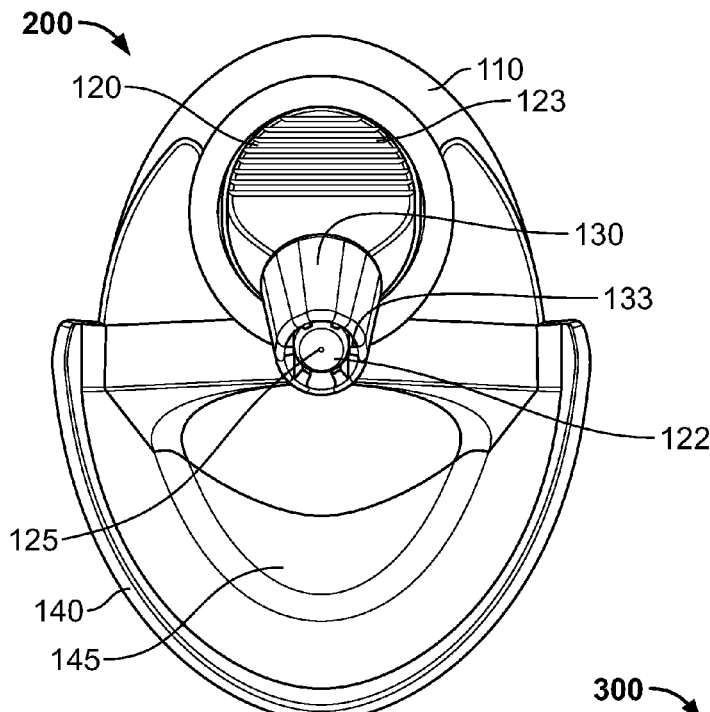
FIG. 2 is a schematic top view of the rinsing assembly shown in FIG. 1.

FIG. 2 is a schematic top view 200 of the rinsing assembly 100 shown in FIG. 1. The top view 200 illustrates a position during fluid application (e.g., the direction out of the page would be the direction placing the rinsing assembly 100 towards a user's ear). The curved contour of the collector 140 can surround the user's ear and be pressed against a side of the user's ear or face to form a collection zone 145. The rinsing fluid exiting the ear canal or the tip portion 122 of the actuator 120 can be substantially enveloped by the collection zone 145. The collection zone 145 can be shaped to include a bucket portion to hold the collected rinsing fluid.

The actuator 120 includes a gripping portion 123 and an aperture 125 at the tip portion 122. The gripping portion 123 can be formed with a non-slip (e.g., corrugated) surface allowing a user's fingers to securely press down the actuator 120 without slipping. The aperture 125 can include one or more holes for dispensing the rinsing fluid. As illustrated in FIG. 2, the channel support 130 is placed near and surrounding the tip portion 122 of the actuator 120. Between the tip portion 122 of the actuator 120 and the channel support 130, a number of fluid channels 133 can be provided. The fluid channels 133 can allow used rinsing fluid to travel out of the ear canal and be directed to the collection zone 145.

Figure 3:
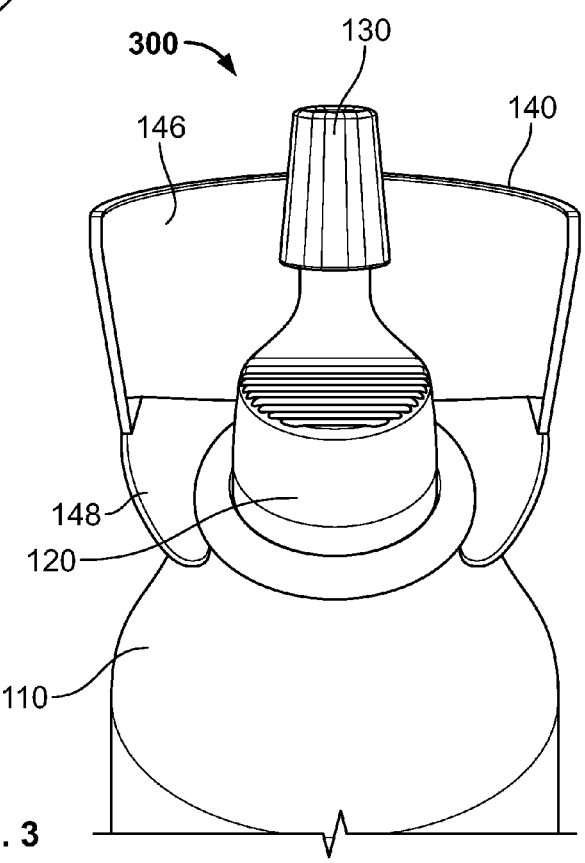
FIG. 3 is a partial perspective view of the rinsing assembly shown in FIG. 1.

FIG. 3 is a partial perspective view 300 of the rinsing assembly 100 shown in FIG. 1. The partial perspective view 300 can be perceived as a top view looking down at the rinsing assembly 100 during a rinsing operation (e.g., when the rinsing assembly 100 is held approximately horizontally for inserting the channel support 130 into an ear canal).

A complete earwax removal operation can include dissolving earwax using an earwax removal solution (either dispensed from the rinsing system 100 or separately provided into the ear canal). A user can tilt the treated ear canal upward to hold the earwax removal solution for a short period of time (e.g., few minutes), and downward to force, by gravity, the solution to exit the ear canal along with rinsing fluid (e.g., so as to enable the rinsing fluid to flush out the earwax together with the earwax removal solution).

As discussed above, the rinsing fluid can be mixed with the earwax removal fluid in the ear canal (or pre-mixed in the sealed housing 100) and exit the channels 133 of the channel support 130. The exiting fluids can flow directly into the collection zone 145 of the collector 140 along a receiving surface 146. The collector 140 can form a sealed region or wall with the user's ear/face by pressing the outer edge of the collector 140 towards the user's ear/face. The outer edge of the collector 140 conforms to the contour of a human ear and can fit with the facial contour of the user. The receiving surface 146 can be approximately horizontal to collect both dripping and flowing exiting fluids.

In some implementations, the collector 140 can be removably attached to the sealed housing 110. As illustrated in FIG. 3, the collector 140 includes an arc-shaped attachment plate 148 that attaches (e.g., clamps) to the sealed housing 110. Although FIG. 3 shows the collector 140 as removably attached to the sealed housing 110, other implementations are possible. In some implementations, the collector 140 can be an integral part of the channel support 130 to form a single unitary assembly. For example, the channel support 130 can be extended to be integrated with the collector 140. In some implementations, the collector 140 can be an integral part of the sealed housing 110. For example, the sealed housing 110 can be manufactured to include the collector 140.

Figure 4:
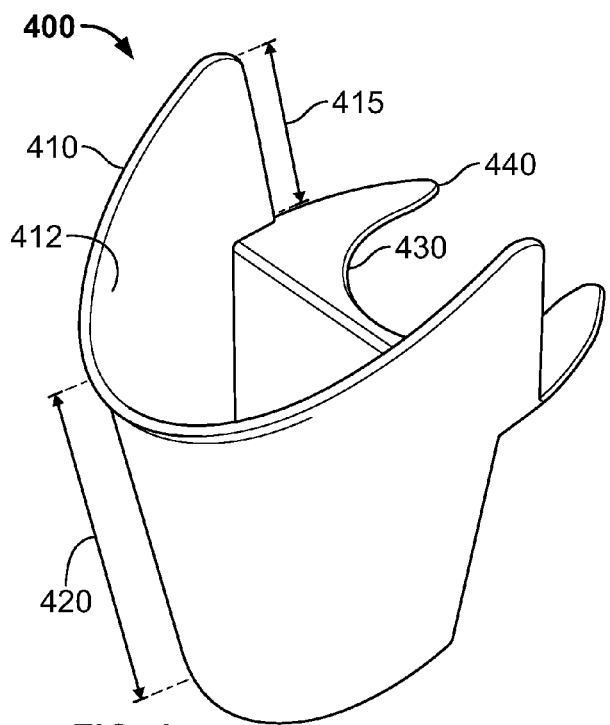
FIG. 4 is a schematic perspective view of a fluid collector.

FIG. 4 is a schematic perspective view of a fluid collector (e.g., fluid collector 400). The fluid collector 140 of FIG. 1 can be of the form of fluid collector 400. The fluid collector 400 includes a contact edge 410, a dimensional spacing element 415, a collection zone 412 (e.g., similar to collection zone 145), and an attachment plate 440. The contact edge 410 can be pressed against a user's ear/face during operation and prevents rinsing fluids from dripping or splashing out of the collection zone 412. The collection zone 412 has a depth 420 for holding used rinsing fluids. The depth 420 can be between 25 mm (or approximately 1 inch) to 100 mm (or approximately 4 inches), to facilitate portability and convenience. In some implementations, when the depth 420 does not provide enough capacity for holding the used rinsing fluids, the fluid collector 400 can be detached from the rinsing assembly 100 to allow the used rinsing fluid to be discarded. The collection zone 412 can be configured to have a tilting angle defined in part by the dimensional spacing element 415. For example, a larger dimensional spacing can result in a larger tilting angle with respect to the ear canal so as to allow the fluid collector 400 to hold more used rinsing fluids. Increasing the tilt angle may have the effect of decreasing the coverage for potential spill or splash. The fluid collector 400 can further include an attachment plate 430 defining a mounting collar. In some implementations, the attachment plate 440 can be flexible and elastically deformable for mounting on a sealed housing.

Figure 5:
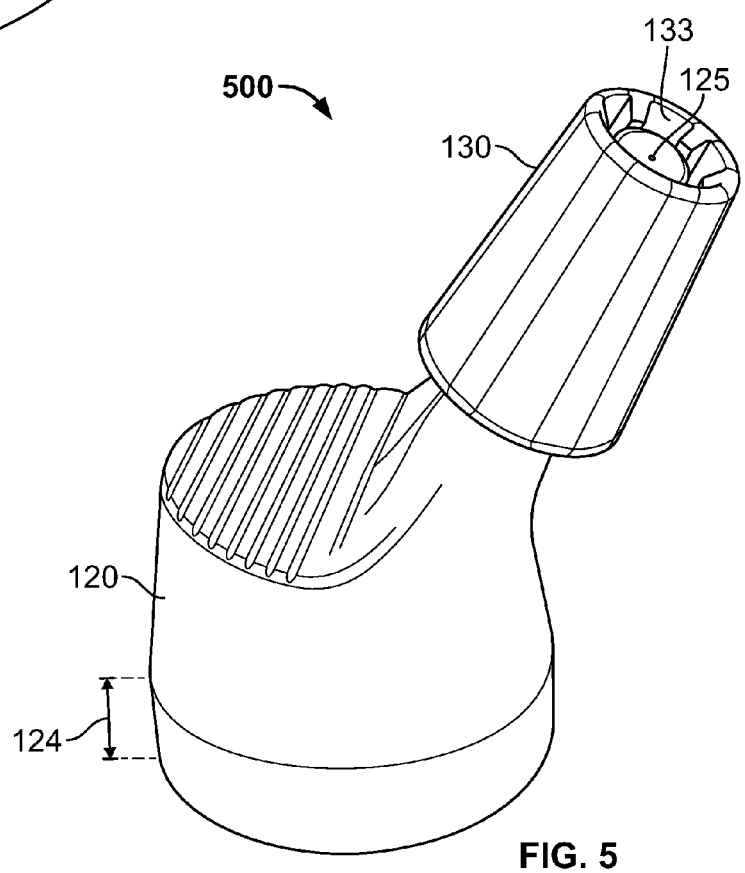
FIG. 5 is a schematic perspective view of a fluid actuator assembly.

FIG. 5 is a schematic perspective view of a fluid actuator assembly 500. The assembly 500 includes the actuator 120 and the channel support 130. The actuator 120 can eject fluid to rinse, cleanse, moisturize, or sooth passages (e.g., ear canals). In some implementations, the actuator 120 also can be designed with a configuration that prevents rinsing solution to re-enter back into the sealed housing through the aperture 125. The actuator 120 also can include a cavity for connecting a conduit in the rinsing fluid housing (e.g., the sealed housing 110 of FIG. 1) to the aperture 125. The cavity can attenuate fluid pressure for a smooth/controlled dispensing operation. The conduit can include a valve that is open when the actuator is actuated to allow the fluid to exit the tip portion 620 (shown in FIG. 6) of the actuator 120. The conduit of the rinsing fluid housing can be an opening, or a tubular structure extending to a certain depth of the rinsing fluid housing. The actuator 120 also can include a bottom portion 124 that aligns the actuator 120 with the rinsing fluid housing and enables a guided displacement during actuation. In some implementations, the bottom portion 124 is tapered or shaped to facilitate connection to the housing 110 or otherwise facilitate fluid flow.

Figure 6:
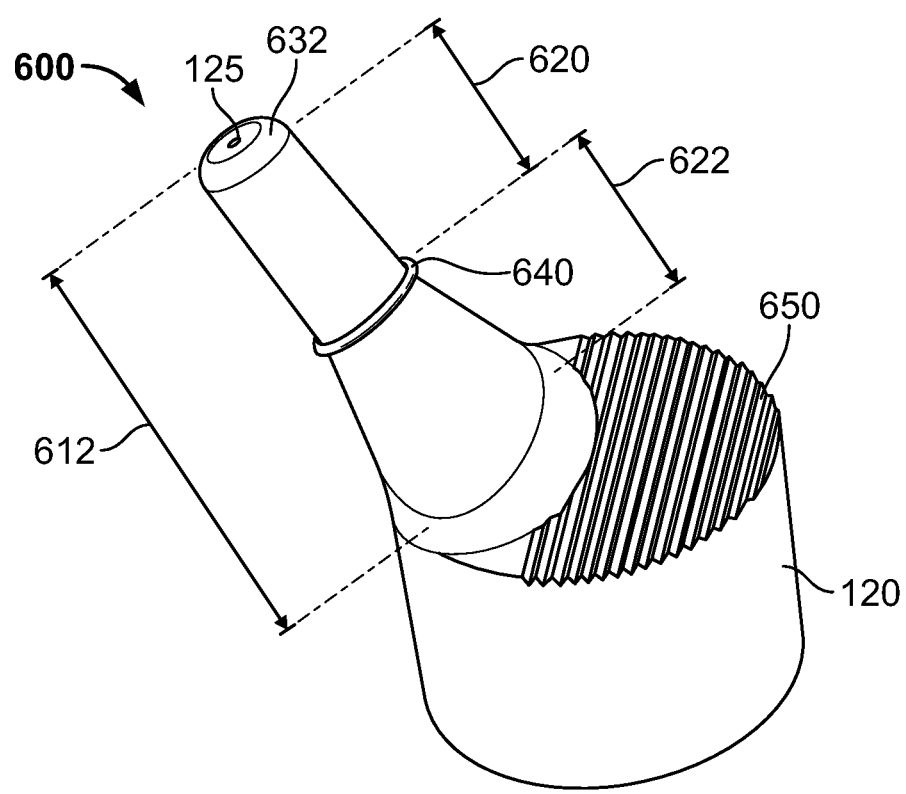
FIG. 6 is a schematic perspective view of a fluid actuator.

FIG. 6 is a schematic perspective view 600 of an example of the fluid actuator 120. The fluid actuator 120 can eject fluid to rinse, cleanse, moisturize or sooth passages (e.g., ear canals). The actuator 120 includes a textured body structure 650 and a tip 612 that includes an upper portion 620 and a proximate portion 622. The upper portion 620 can be designed with dimensions that allow the upper portion 620 to be completely inserted into a user's ear canal. For example, the upper portion 620 can be a cylindrical shape that has a diameter smaller than an average size of human ear canals. At the end of the upper portion 620, the aperture 125 is provided on a mesa 632. The proximate portion 622 connects the upper portion 620 to the body structure and operates with an inner cavity to generate desired fluid pressure and volume. In some implementations, the actuator 120 can be configured to attenuate the fluid pressure further for ejection of a medium stream through the aperture 125.

In some implementations, the fluid actuator 120 can include an attachment ridge 640 at or in a vicinity of the proximate portion 622 for attachment of/to the support channel 130. For example, the support channel 130 can securely mate onto/over the proximate portion 622 at the attachment ridge 640.

Figure 7A:
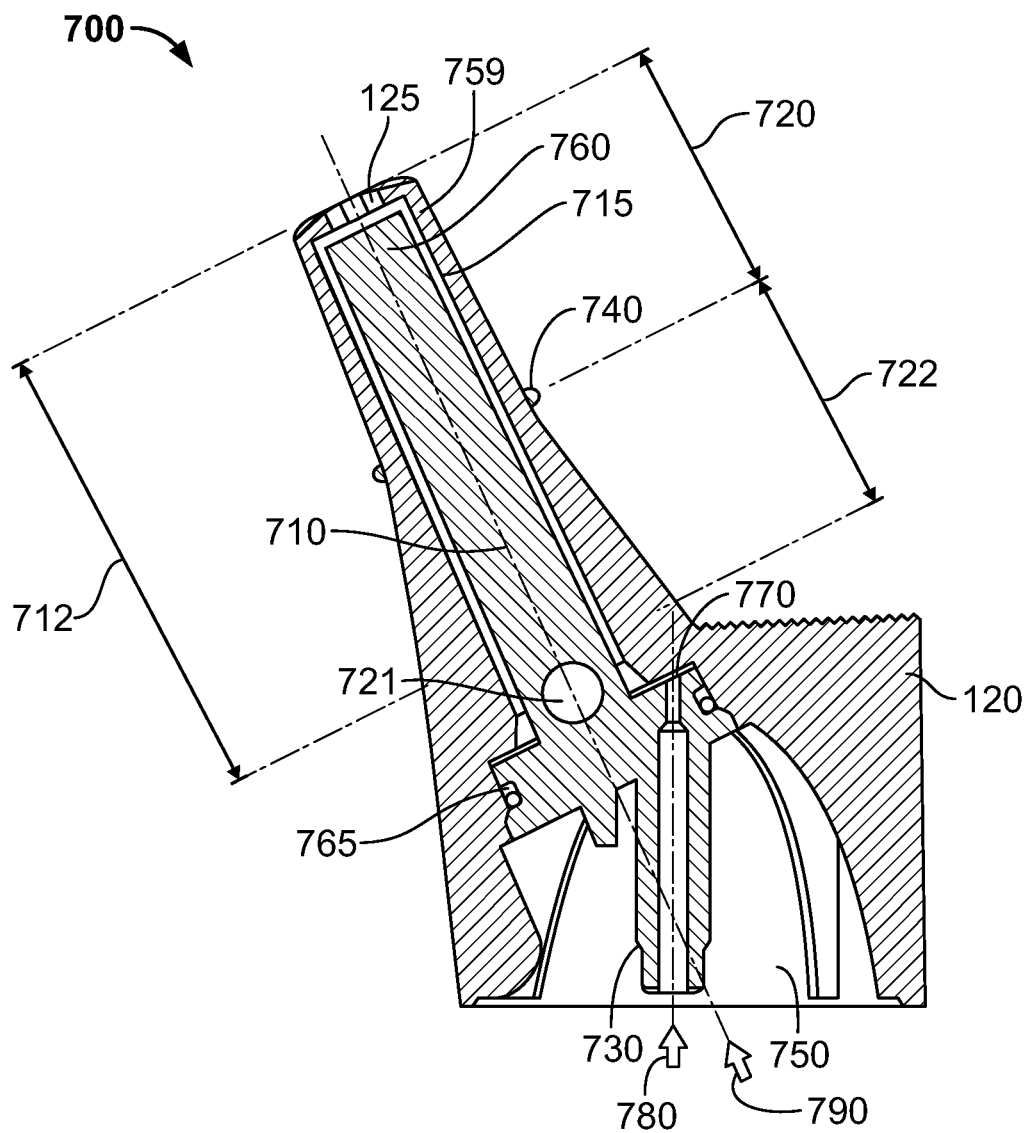
FIG. 7A is a cross sectional side view of an example of a fluid actuator.

FIG. 7A is a cross sectional side view 700 of an example of the fluid actuator 120. From the view 700, the actuator 120 includes an external shell 759 and an internal component 760. The tapered shape of the tip 712 is shown to include the tapered surface that extends along the tip portion 720 (similar to the tip portion 620 of FIG. 6) toward its intersection with the proximate portion 722. The view 700 further shows a cross-section of the features of the interior 750 of the actuator 120. Fluid can flow through the tip 712 by entering a base tube 730 of the inner component 710. For example, the base tube 730 can couple with a sealed housing containing rinsing fluid and be actuated by displacing downwards to open a valve of the conduit of the sealed housing and to release pressurized fluid through the conduit. Fluid dispensed from within the sealed housing can flow through the base tube 730 and through the interior 760 of the tip 712, exiting through the distal end of the tip portion 720.

A canal 715 in the interior of the tip 712 can provide fluid connectivity between the tube 730 and the aperture(s) 125 of the actuator 120. The canal 715 is formed from the clearance between the inner chamber of the tip 712 and the extruding portion of the inner component 710. In some implementations, the shape of the inner chamber of the tip 712 and the extruding portion of the inner component 710 can be identical or of different sizes. For example, the inner chamber of the tip 712 can be of a cylindrical shape but slightly larger than that of the extruding portion of the inner component 710. Specifically, the canal 715 can extend from the aperture(s) 125 to the most distal position of the proximate portion 722.

The component 760 includes an extrusion portion 760, a sealing portion 765, and the base tube 730. In this example, the extrusion portion 760 is shaped as a tapered cylinder with the base portion connecting to the sealing portion 765 wider than the tip portion. In some implementations, the extrusion portion 760 can be substantially 26 mm in length. The tip of the extrusion portion 760 can be a circular mesa of a substantially 4 mm diameter. The extrusion portion 760 can taper at substantially 2 degrees and increase its cross-sectional diameter towards the sealing portion 765. Approximately tangential to the sealing portion 765, a cylindrical cavity 721 is formed inside the extrusion portion 760. The cavity 721 extends in a direction as shown in FIG. 7, but it may also extend in other directions. The cavity 721 can be a cylindrical shape of substantially 3 mm diameter.

The sealing portion 765 can couple with the internal chamber 750 of the actuator 120 to form the passage that allows fluid to flow from the base tube 730 to the aperture(s) 125. The sealing portion 765 includes a stepped structure for sealing and an orifice 770 connected to the base tube 730 for attenuation and regulation of the fluid pressure. The stepped structure may include a groove that can receive a rubber ring for improved sealing. In some implementations, the orifice 770 can be a cylindrical hole of substantially 0.6 mm diameter, connected to the internal cylindrical portion of the base tube 730. The internal cylindrical portion of the base tube 730 can be substantially 1.5 mm in diameter and about 13 mm in total length. A gradual transition, such as a chamfer or a rounded step, may exist at the connection between the orifice and the inner cylindrical portion. The external diameter of the base tube 730 can be substantially 3.5 mm in diameter, or any dimension that ensures the structural integrity to withstand internal pressure as well as external compression loading.

During operation, a user may press down the actuator 750 by asserting a force towards the sealed housing containing rinsing fluid (e.g., the housing 110). As the actuator displaces towards the housing, pressurized fluid ejects from the housing into the base tube 730. Simultaneously, the compression against the housing allows the actuator 120 to form a seal with the inner component 710 at the sealing portion 760. The fluid travels through the inner cylindrical portion of the base tube 730 into the orifice 770, then into the canal 715. The cavity 721 may serve as a buffer for pressure release as well as a reservoir storing extra fluid. After the canal 715 and the cavity 721 are filled with the fluid, the fluid can be ejected through the aperture(s) 125 at an attenuated pressure. In some implementations, similar to the attachment ridge 640 of FIG. 6, an attachment ridge 740 can be placed between the tip portion 720 and the proximate portion 722 for attaching a channel support.

Figure 7B:
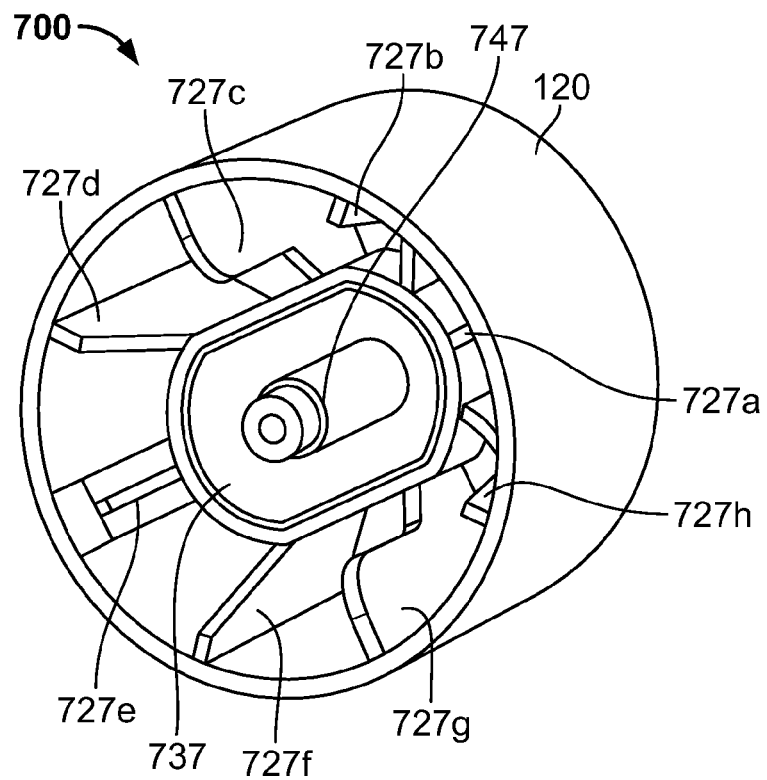
FIG. 7B is a schematic perspective bottom view of the fluid actuator shown in FIG. 7A.

FIG. 7B is a schematic perspective bottom view of the fluid actuator 120 presented in FIG. 6. The bottom view is shown in the direction that is parallel to the longitudinal axis of the extrusion portion 760. In some implementations, FIG. 7 shows exemplar rib designs regarding each relative position to the external shell 759. For example, rib 727a has an arc shape due to its furthest distance from the housing 737. The rib 727c and 727g extends vertically so that attaching to another structure is made possible. The rib 727e is shorter than others but reinforced by additional structure connected to the inner wall of the external shell 759 to give enough support to the external shell 759. Depending on the material used, the rib design may vary without geometric limitation when performing the same structural function.

Figure 8:
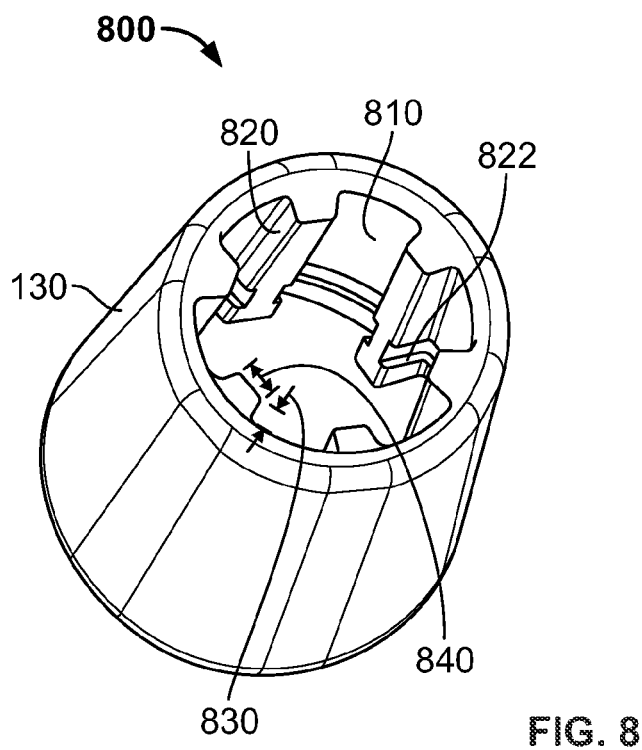
FIG. 8 is a schematic perspective view of a fluid channel support.

FIG. 8 is a schematic perspective view 800 of an example of the fluid channel support 130. The channel support 130 can include a number of channels 810 formed by a number of rails 820. The channel support 130 can be a cylindrical shape that conforms to the contour of the tip portion 620 of the actuator 120. The rails 820 can be in direct contact with the tip portion 620 when the channel support 130 is securely attached onto the actuator 120. The channels 810 can provide fluid flow space between the inner wall of the channel support 130 and the exterior surface of the actuator 120 at the tip portion 622. The rails 820 support the inner wall of the channel support 130. For example, when the tapered channel support 130 is partially inserted into an orifice to be rinsed (e.g., into an ear canal), the orifice can compress the channel support 130 inwards. The inward deformation of the channel support 130 can be limited by the rails 820 (i.e., the rails 820 are supported by the tip portion 620 of the actuator 120, resisting further deformation). Therefore the fluid passage space of the channels 810 can be substantially retained for the intended operation (e.g., to enable a non interfering exit path for the fluid that is returned from the orifice).

In some implementations, the channels 810 can include a large opening for high volume dispensing. In some implementations, the number of channels 810 can be determined by the rail 820's width 840. The size of the channel can be determined for example by a combination of the rail 820's height 830 and width 840, for example, the larger the height 830 and the smaller the width 840, the larger the individual channel 810. In the embodiment illustrated in FIG. 8, the height 830 and the width 840 are approximately 1 mm. In some implementations the channel can be uniform over its length. In some implementations the channel can be tapered (either to narrow or widen the channel over its length). An attachment channel 822 traversing the support rails 820 can be included for coupling with the attachment ridge (e.g., the attachment ridge 640 of FIG. 6, or 740 of FIG. 7) of the actuator 120. The attachment channel can be perpendicular to the rails 820 and secure the channel support 130 from moving up and down relative to the actuator 120 (e.g., the channel support 130 may still rotate freely with respect to the actuator 120).

During operation, a user can tile his/her head sideways, and place a predetermined number of ear wax removal drops (e.g., five to ten drops) into each ear canal. The removal drops can remain in the ear for a predetermined period of time (e.g., three, five, or ten minutes) by keeping the head tilted or placing an ear plug in each ear (where the ear plugs can be removed upon expiration of the predetermined period). As the user removes the ear plug in each ear, the collector 140 can be used to "catch" the removal drops dripping out of the ear. The ears can then be rinsed after treatment by gently flushing the ear with A number of embodiments of the invention have been described. Nevertheless, it will be understood that various modifications may be made without departing from the spirit and scope of the invention. For example, instead of attenuating a fast stream of liquid into a gentle flow, a mist exiting the actuator can be transformed into a gentle cleansing stream of fluid. Accordingly, other embodiments are within the scope of the following claims.

What is claimed is:

1. An assembly comprising:
   a housing containing fluid, the housing comprising a conduit;
   an actuator operationally attached to the conduit of the housing, the actuator comprising:
   a body portion surrounding a cavity;
   a tip portion having a fluid path that is fluidly connected to the cavity, the cavity being fluidly connected to the conduit, and
   a channel support including a plurality of support rails in direct contact with an exterior surface of the tip portion when the channel support is securely attached to the actuator, wherein a fluid passage space is defined between adjacent support rails of the plurality of support rails, an inner wall of the channel support, and the exterior surface of the actuator, and wherein the channel support is configured for insertion into an ear canal; and
   a fluid collector having a collection zone configured to collect fluid dispensed from the tip portion.

2. The assembly of claim 1, wherein the conduit includes a valve that is open when the actuator is actuated to allow the fluid to exit the tip portion.

3. The assembly of claim 1, wherein the actuator is configured to attenuate a predetermined pressure level of the fluid when the actuator is actuated.

4. The assembly of claim 3, wherein the fluid is dispensed at the predetermined pressure sufficient to deliver the fluid to the ear canal without the pressure being so great as to displace an eardrum.

5. The assembly of claim 4, wherein the actuator is configured to attenuate fluid flow of the fluid at a plurality of different pressure levels.

6. The assembly of claim 1, wherein the plurality of support rails prevent the inner wall of the channel support from contacting the tip portion.

7. The assembly of claim 6, wherein the channel support includes an attachment channel traversing the plurality of support rails, the attachment channel operable to engage with an attachment ridge of the tip portion.

8. The assembly of claim 1, wherein the tip portion includes a base tube coupled with the body portion, the base tube actuated when displaced downward to open a valve for releasing pressurized fluid in the body portion.

9. The assembly of claim 8, wherein the tip portion includes a sealing portion coupled with the actuator to form the fluid path and configured to seal fluid from communicating from the base tube to one or more apertures in the tip portion.

10. The assembly of claim 1, wherein a contact edge of the detachable fluid collector includes a curved plate conforming to a general ear shape and operable to engage with a portion of a subject's ear or face to form a sealed wall.

11. The assembly of claim 1, wherein the collection zone includes a sealed wall, a collection surface of the collector, and a liquid container.

12. The assembly of claim 1, wherein the channel support directs a portion of used fluid towards the collection zone.

13. A system comprising:
   an actuator comprising:
   a body portion surrounding a cavity;
   a tip portion having a fluid path that is fluidly connected to the cavity, the cavity being fluidly connected to a reservoir; and
   a channel support including a plurality of support rails in direct contact with an exterior surface of the tip portion when the channel support is securely attached to the actuator, wherein a fluid passage space is defined between adjacent support rails of the plurality of support rails, an inner wall of the channel support, and the exterior surface of the actuator, and wherein the channel support is configured for insertion into an ear canal; and
   a fluid collector comprising:
   an edge configured to surround a subject's ear and fittingly rest on an area near the ear; and
   a collection zone extending from the edge, the collection zone configured to receive fluid dispensed by the actuator.

14. The system of claim 13, further comprising a housing configured to store the reservoir, the housing comprising a conduit fluidly connecting the reservoir to the cavity.

15. The system of claim 13, wherein the actuator is configured to attenuate a predetermined pressure level of the fluid when the actuator is actuated.

16. The system of claim 13, wherein the plurality of support rails prevent the inner wall of the channel support from contacting the tip portion.

17. The system of claim 13, wherein the collection zone includes a sealed wall, a collection surface of the collector, and a liquid container.

18. The system of claim 13, wherein the channel support directs a portion of used fluid towards the collection zone.

19. The system of claim 1, wherein the channel support conforms to an outer contour of the tip portion.

20. The system of claim 13, wherein the channel support conforms to an outer contour of the tip portion.

\* \* \* \* \*